US012490960B2

(12) United States Patent
Ezkerra et al.

(10) Patent No.: US 12,490,960 B2
(45) Date of Patent: Dec. 9, 2025

(54) DEVICE AND METHOD FOR TAKING UP AND HANDLING A LIQUID SAMPLE AND A SUBSTANCE

(71) Applicant: Anvajo Gmbh, Dresden (DE)

(72) Inventors: Aitor Ezkerra, Dresden (DE); Daniel Hammer, Dresden (DE)

(73) Assignee: Anvajo GmbH, Dresden (DE)

( * ) Notice: Subject to any disclaimer, the term of this patent is extended or adjusted under 35 U.S.C. 154(b) by 992 days.

(21) Appl. No.: 17/600,330

(22) PCT Filed: Mar. 31, 2020

(86) PCT No.: PCT/EP2020/059044

§ 371 (c)(1),
(2) Date: Sep. 30, 2021

(87) PCT Pub. No.: WO2020/201250

PCT Pub. Date: Oct. 8, 2020

(65) Prior Publication Data

US 2022/0167951 A1 Jun. 2, 2022

(30) Foreign Application Priority Data

Apr. 2, 2019 (DE) ..................... 10 2019 204 633.9

(51) Int. Cl.
*A61B 10/00* (2006.01)
*B01L 3/00* (2006.01)

(52) U.S. Cl.
CPC .......... *A61B 10/0045* (2013.01); *B01L 3/502* (2013.01); *B01L 2300/042* (2013.01);
(Continued)

(58) Field of Classification Search
CPC . A61B 10/0045; A61B 10/0096; B01L 3/502; B01L 2300/042; B01L 2300/045;
(Continued)

(56) References Cited

U.S. PATENT DOCUMENTS

2012/0325721 A1 12/2012 Plante et al.
2013/0092690 A1 4/2013 Skakoon
(Continued)

FOREIGN PATENT DOCUMENTS

GB 2459122 A 10/2009
JP S6378454 U 5/1988
(Continued)

OTHER PUBLICATIONS

European Patent Office, International Search Report and Written Opinion in Application No. PCT/EP2020/059044, dated Jun. 24, 2020, 12 pages, Rijswijk, Netherlands.
(Continued)

*Primary Examiner* — Patrick Fernandes

(74) *Attorney, Agent, or Firm* — Marshall & Melhorn, LLC

(57) ABSTRACT

A device and a method for taking up and handling a liquid sample and a substance are described. The device has a sample unit and a substance container. The substance container has a reservoir which is designed to keep a substance in the reservoir. The reservoir also has an opening which is closed by a sealing film or sealing plate so that substance kept in the reservoir is sealed with respect to the surroundings. The sample unit is equipped with a sample taker which is designed to take up and hold a liquid sample. It also has an opener which is designed to be at least partially inserted into the opening of the reservoir and to lift the sealing film or sealing plate from the opening.

11 Claims, 4 Drawing Sheets

(52) U.S. Cl.
CPC ... *B01L 2300/045* (2013.01); *B01L 2300/047* (2013.01); *B01L 2300/0832* (2013.01)

(58) Field of Classification Search
CPC ....... B01L 2300/047; B01L 2300/0832; B01L 2300/044; B01L 2300/0672; B01L 220/16
See application file for complete search history.

(56) References Cited

U.S. PATENT DOCUMENTS

| | | | |
|---|---|---|---|
| 2018/0193830 | A1 | 7/2018 | Nishikawa et al. |
| 2018/0272330 | A1 | 9/2018 | Lee et al. |

FOREIGN PATENT DOCUMENTS

| | | | |
|---|---|---|---|
| JP | H021627 | U | 1/1990 |
| WO | 2016079611 | A1 | 5/2016 |

OTHER PUBLICATIONS

Japanese Patent Office, Office Action In Application No. JP2021-558917, dated Sep. 9, 2024, 6 pages.

DEVICE AND METHOD FOR TAKING UP AND HANDLING A LIQUID SAMPLE AND A SUBSTANCE

FIELD

The invention relates to a device for taking up and handling a liquid sample and a substance. The device is in particular suitable for sample analysis in the medical, pharmaceutical, or biological sectors.

BACKGROUND

It is frequently necessary for the analysis of liquid samples to subject a certain amount of a liquid sample to various analysis steps. For this purpose, liquid samples are typically taken up by a pipette or by another suction device that generates a vacuum and are transferred into a vessel in which the analysis steps are carried out. The samples can then, for example, be mixed with other substances.

In a large number of cases, corresponding equipment and aids for providing the samples or substances such as pipettes, pipetting aids, tubes, pumps, weighing boats, or scales are not present at the place of use or analysis or operating errors occur in the use so that the taking up and handling of the samples and/or of the substances is not reproducible. The equipment and aids for providing the samples and substances also have to be disposed of or cleaned in a complex and/or expensive manner after the taking up and providing of the samples or substances to avoid contamination. A particular challenge in this respect is the reproducible taking up and handling of a sample having a volume in the microliter range since even small differences in the sample volume or small amounts of contaminants can result in large errors in the analysis results.

SUMMARY

It is therefore the underlying object of the present invention to overcome said disadvantages and to provide an inexpensive device that is simple to operate and a method for taking up and handling a liquid sample and a substance. A device should in particular be provided as a mass-produced article or disposable article with which a liquid sample in the microliter range can be reproducibly taken up and can be made accessible to a large number of different analysis steps, inter alia mixing with a substance.

This object is achieved in accordance with the invention by a device and by a method in accordance with the claims. Advantageous embodiments and further developments are described in the dependent claims.

A device for taking up and handling a liquid sample and a substance has a sample unit having an opener and a sampler that is configured to take up and hold a liquid sample. In addition, the device has a substance container having a reservoir that is configured to store a substance in the reservoir. The reservoir has an opening that is closed by a sealing film or a sealing plate so that the substance stored in the reservoir is sealed toward the environment. The opener of the sample unit is configured to be at least partially introduced into this opening of the reservoir and to raise the sealing film or sealing plate from the opening. In this respect, a surface of the opener that is arranged in the direction of the sealing film or sealing plate and that is introduced into the opening and raises the sealing film or sealing plate from the opening is configured such that the surface is aligned at an oblique angle to the surface of the sealing film or sealing plate on contact with the sealing film or sealing plate and raises the sealing film or sealing plate successively from the opening on the introduction into the opening so that an outlet is formed in the sealing film or sealing plate through which the substance exits the reservoir and is miscible with the sample of the sampler.

Due to the integrated sampler, no separate equipment or aids are required in addition to the device for the taking up of the liquid sample. This has the advantage that the device can be used independently for taking up samples at the deployment site. In addition, a contamination of the sample by separate pieces of equipment or aids for taking up the sample is precluded and the cleaning of these pieces of equipment or aids can be dispensed with.

Contamination of the substance, but also contamination of the environment can be avoided by the provision of the substance in a sealed reservoir. In particular hazardous substances such as biohazards or carcinogenic substances can be safely transported and handled with the device without any uncontrolled contact with the environment. The reservoir can additionally be filled and emptied at different locations. It can, for example, be filled and closed in a sterile environment by means of high precision devices to then be used in the device at a different location. The measurement error on the filling of the substance container can thereby be reduced, on the one hand, and the device can be used independently of equipment or aids for filling, on the other hand.

The reservoir can be fillable or filled with a solid, liquid, and/or gaseous substance, in particular a fluid or a plurality of fluids such as a flowable liquid, a flowable or free-flowing solid such as a powder, granulate, or agglomerate, or mixtures thereof. A viscous substance such as a gel or a paste or a solid substance can, however, also be taken up that can be flushed out of the reservoir by means of the sample or by another liquid.

The oblique angle between the sealing film or sealing plate and the surface at the opener that is introduced into the opening of the reservoir and raises the sealing film or sealing plate from the opening prevents an uncontrolled tearing of the sealing film or sealing plate. Instead of tearing in an uncontrolled manner and being urged to the side sectionwise, the sealing film or sealing plate is successively raised from the opening as a contiguous surface so that the outlet that is produced can be completely used for the release of the substance from the reservoir. A single linear movement of the opening is typically already sufficient for this; it can in particular take place in a normal direction of the opening surface of the opening that is for this purpose as a rule guided in parallel with the normal direction of an end surface of the sampler. The surface of the opener that is introduced into the opening of the reservoir and that raises the sealing film or sealing plate from the opening preferably forms an angle on contact with the sealing surface or sealing plate between 5° and 45°, preferably 5° and 30°, particularly preferably 5° and 20°, to the surface of the sealing film or sealing plate.

Provision can be made that the surface of the opener that is introduced into the opening of the reservoir and that raises the sealing film or sealing plate from the opening is configured to raise the sealing film or sealing plate successively starting from the margin of the opening. This has the advantage that the sealing film or sealing plate raised by the opener is moved on the introduction of the opener into the opening to the side wall of the opening or to the inner wall of the reservoir and thereby only represents a vanishingly small flow resistance on the release of the substance from the reservoir. The reservoir can thus be emptied fast and completely. The possibility is in particular favorable here that the sealing film or sealing plate is raised successively as a contiguous surface from the total opening on the introduction of the opener into the opening and can be moved to the side wall or inner wall of the reservoir or can be folded over and fixed by the opener there. The flow resistance of the sealing film or sealing plate can thereby be reduced on the release of the substance from the reservoir.

It is advantageous if the opener has a tip, a pricker, a piercer, or a cutting edge by which the sealing film or sealing plate is cut on contact with the sealing film or sealing plate. The pressure that has to be applied to cut the sealing film or sealing plate for the raising can thus be reduced by the tip, the pricker, the piercer, or the cutting edge and the release of the substance can thus be facilitated. An uncontrolled tearing, but also an unwanted inward arching and rolling together of the sealing film or sealing plate can furthermore be avoided.

At least one tip, one pricker, or one piercer is preferably arranged at the position of the opener that first contacts the sealing film or sealing plate on the introduction of the opener into the opening. The cutting edge is preferably formed at the margin of the surface of the opener that is introduced into the opening and that raises the sealing film or sealing plate from the opening. The cutting edge can in particular be formed with a one-sided or two-sided, flat, spherical, hollow, or concave cutting geometry. Provision can in addition be made that the cutting edge has cutting teeth or a microchamfer that enables a particularly clean cut.

The opener of the sample unit is preferably formed in a complementary shape to the opening of the reservoir into which it is introduced to raise the sealing film or sealing plate, i.e. the opener is in particular formed in a matching shape or with an exact fit with respect to the opening. The sealing film or sealing plate can thereby be substantially raised over the total cross-section of the opening and can be opened for the release of the substance from the reservoir. The sealing film or sealing plate can additionally be moved on the successive introduction of the opener and the raising of the sealing film or sealing plate to the side wall of the opening and/or to the inner wall of the reservoir and can be fixed by the opener there so that, on a discharge of the substance, it is not moved by it in the direction of the outlet and does not block it. The opener and in particular the surface of the opener arranged in the direction of the sealing film or sealing plate can therefore have an outer contour or an outer edge that is shaped such that, on the introduction of the opener into the opening, a gap is formed between the outer contour and/or the outer edge and a side wall of the opening and/or the inner wall of the reservoir in which the sealing film or sealing plate is fixed. The term fixed in this application can in particular be understood such that the movement of the sealing film or sealing plate is restricted by an outer contour of the opener and the side wall of the opening and/or the inner wall of the reservoir such that, on the discharge of the substance, the sealing film or sealing plate is not moved by it in the direction of the opening. The sealing film or sealing plate can here in particular contact the side wall of the opening and/or the inner wall of the reservoir in a flat manner. The opener and/or the surface of the opener arranged in the direction of the sealing film or sealing plate can be configured, for example, such that the outer contour or the outer edge forms a gap on the introduction of the opener into the opening whose clearance amounts to 1.5 times to 20 times the thickness of the sealing film or sealing plate, preferably 5 times to 10 times the thickness of the sealing film or sealing plate.

The reservoir is preferably formed as a cavity that is open at one side so that a cross-sectional surface that is as large as possible can be produced for the release of the substance from the reservoir by the opening of the sealing film or sealing plate. This has the advantage that even viscous or solid substances can be released in a fast and uncomplicated manner from the reservoir by a flushing by means of the sample or another liquid. The opening in the reservoir is particularly preferably formed at the lower side of the reservoir or of the substance container so that an unimpeded discharge of the substance by means of gravity is possible.

It is advantageous if the opener that is introduced into the opening of the reservoir has at least one passage and/or at least one outlet opening through which the substance can exit the reservoir on the raising of the sealing film or sealing plate. The opener is particularly preferably formed as a planar surface structure or as an interrupted hollow body or as a ring or in ring shape. It can thereby be avoided that the opener prevents the substance from exiting through the outlet. The substance can already exit the reservoir during the penetration of the sealing film or sealing plate. Provision can also be made to configure the opening as a hollow cylinder chamfered at one side. It is additionally possible to connect the opener to the sampler via a web or a plurality of webs to obtain an arrangement in which openings for a throughflow are still present despite a mechanically secure connection via webs. Provision can in particular be made that the opener is configured as a ring that is connected to the sampler via webs. The term "ring" should here in particular be understood as a uniformly round article closed in itself of any desired width and/or length. A more homogeneous distribution of the exiting substance can moreover be achieved by outlet openings that are aligned in different spatial directions, which in particular promotes the mixing of the substance with a sample in the region of the opener. The term "web" should in particular be understood within the framework of this application as a connection part that, however, does not completely fill and/or cover a space between two elements to be connected by this web.

The sampler can be designed as a capillary tube that is configured to take up a defined sample amount in it by means of capillary forces. Capillary tubes are inexpensive and failsafe samplers since they do not require either electronic or mechanically moved components. Due to the small opening cross-section of the capillary tubes, solids can hardly penetrate into the capillary tubes so that the sample can very largely be taken up without contamination. Typical diameters and capacities of the capillary tubes amount to between 0.02 mm and 2 mm and 1 μl to 100 μl.

The sampler is preferably arranged disposed opposite the opener at the sample unit. For liquid substances, the sampler can, for example, be arranged centrally to the surface of the opener that is introduced into the opening of the reservoir and that raises the sealing film or sealing plate from the opening so that on the exit of the substance from the reservoir, it can be flowed around or through by it and an intermixing of the substance with the sample from the sampler is facilitated. For flowable or free-flowing substances, the sampler can also be arranged laterally offset from the center of the surface that is introduced into the opening of the reservoir and that raises the sealing film or sealing plate from the opening so that the substance does not block the sampler on exiting the reservoir.

The sampler and the opener can be formed as a contiguous unit. The sampler can, for example, be connected to the opener via webs, with the webs having a cross-section that is as narrow as possible, preferably narrower than 2 mm, so that they do not impede the discharge of the substance from the reservoir. The webs can have an outer contour that is shaped in a complementary manner, and preferably with an exact fit, with respect to a side wall of the opening and/or the inner wall of the reservoir. At least one web can particularly preferably be arranged at the opener in a region in which the surface of the opener has a maximum distance from the opening on a contact with the sealing film or sealing plate so that, on the introduction of the opener into the opening, the sealing film or sealing plate is moved and fixed by this web at the side wall of the opening and/or at the inner wall of the reservoir.

Alternatively, the sampler can also have a modular setup so that, for example, different samplers can be fixed to the sample unit by means of a shape matched or force fit or friction locked through hole connection. Provision can also be made in an embodiment, that the sample unit has a plurality of samplers so that different liquids or larger amounts of liquids can be taken up.

Provision can additionally be made for an uncomplicated handling of the device that the substance container is fastenable to the sample unit and the substance container or the sample container is configured to introduce the opener only by means of a compressive movement or rotational movement at the substance container or at the sample unit and to raise the sealing film or sealing plate from the opening. The device can thus be transported or handled as a unit of substance container and sample unit and can only release the substance as required.

Provision can in particular be made that the device has a fastening and release device by which the substance container is fastenable to the sample unit such that the relative movement of the substance container with respect to the sample container is blocked for the introduction of the opener into the opening of the reservoir and for the raising of the sealing film or sealing plate and is only released after an actuation of the release device. The fastening and release device can, for example, be configured as a latching device having a releasable click-in or snap-in mechanism or as a screw connection having a latching mechanism such as a pin, a stud, a splint, or a lever that only releases the relative movement of the substance container with respect to the sample container for the introduction of the opener into the opening and the raising of the sealing film or sealing plate only after its removal or actuation. The release device is preferably operable purely manually, with a mechanical child-proof securing of the release device also being able to be provided for certain applications.

The device, in particular the sample units, preferably also has a connection point at which a container can be fastened that surrounds the sampler and the opening of the reservoir. The substance and the sample can e.g. be taken up and mixed with one another in such a container, but the container can also be used to protect the sample from drying out or to provide a liquid for flushing viscous or solid substances from the reservoir.

The connection point is particularly preferably configured to releasably connect the device to standard laboratory vessels, e.g. cuvettes, vessels having a standard ground joint, centrifuging tubes, or Eppendorf vessels, or to laboratory equipment that has a connection point compatible with standard laboratory vessels. The connection point can, for example, be designed for screw connections, latching connections, or snap-in connections. The connection point is particularly advantageously designed for friction-locked push-in or place-on connections so that the device can be fastened to the container in a fast and uncomplicated manner.

The sample unit can, for example, have a jacket, a sleeve, or a ring that is arranged around the opener and that is configured as a connection point. An outer surface of the jacket, of the sleeve, or of the ring can for this purpose be designed, for example, as a sealing surface for a friction-locked fastening of a container that is pushed onto the jacket, the sleeve, or the ring. The jacket, the sleeve, or the ring can additionally form a contact protection that protects the opener from unwanted contacts when the sample unit is placed on a surface or is handled. Provision can furthermore be made that the jacket, the sleeve, or the ring has an outer surface that is designed as a retaining surface for the handling of the sample unit, in particular for the holding of the sample unit during the taking up of the liquid sample.

The jacket, the sleeve, or the ring can be fastened to the opener, for example, by means of narrow webs and can form a unit with the opener. In an embodiment, the jacket, the sleeve, or the ring can have an inner surface that is designed as complementary in shape to an outer surface of the substance container or reservoir so that the sample unit and the reservoir can be sealed toward the environment in a shape matched manner at this surface on the introduction of the opener into the opening of the reservoir and the raising of the sealing film or sealing plate from the opening and an uncontrolled discharge of the substance from the device can be avoided. Instead of or in addition to this sealing, further sealing surfaces can be provided at the substance container or at the sample unit at which the substance container and the sample container can optionally be sealed toward the environment by means of an additional sealing material on the introduction of the opener into the opening of the reservoir and the raising of the sealing film or sealing plate from the opening.

Provision can further be made in an embodiment that the substance container has a plurality of reservoirs and the sample unit has a plurality of openers. The reservoirs and openers can here be arranged in the substance container or at the sample unit such that a respective opener can be introduced into an opening of a reservoir and opens the sealing film or sealing plate of the reservoir. The sample unit can correspondingly have a connection point at which a container can be fastened that surrounds the sampler and the openings of the reservoir. It is thus possible to provide different substances that are only miscible or mixed with one another only after the opening of the sealing film or sealing plate of the respective reservoir.

Provision can in particular be made that the openers have different lengths or are arranged at more different levels at the sample unit so that they have different distances from the plane of the sealing films or sealing plates of the reservoir on the introduction into the openings of the reservoir. The sealing films or sealing plates of the reservoir can thus be opened after one another and independently of one another on the introduction of the openers into the openings of the reservoirs, with the reservoir having the smallest distance between the opener and the sealing film or sealing plate being opened first.

Alternatively, the openers can be designed as of equal length and can be arranged in a plane at the sample unit and the reservoirs or the sealing films or sealing plates of the reservoirs can be arranged at different levels from one another in the substance container so that the sealing films or sealing plates can be opened after one another and independently of one another on the introduction of the openers into the openings of the reservoirs, with the reservoir having the smallest distance between the opener and the sealing film or sealing plate being opened first. The device can correspondingly have a plurality of latching and release units that can be actuated after one another so that the openers can be introduced into the openings of the reservoirs after one another and the substances can be released after one another. Specific orders in which the substances are to be released can thereby be fixed and so confusion or errors in the analysis sequences can e.g. be avoided. The device is additionally particularly suitable for the time-controlled release of substances. The substances can, for example, be released manually or automatically at certain time intervals.

The sample unit, the substance container, and the sealing film or sealing plate for sealing the reservoir typically consists of materials that enable a long-term storage of the substance or of the sample, i.e. that are chemically or thermally resistant, respectively, and where necessary protect the substance or sample from environmental influences such as UV radiation, humidity, or oxygen. The sample unit or the substance container can be manufactured from plastics, e.g. from thermoplastics such as polypropylene, polyethylene, polyethylene terephthalate, polystyrene, cyclic olefin polymers or copolymers, acrylonitrile butadiene styrene, polyether ether ketone, polycarbonate, polyamides, in particular nylon, polyoxymethylene, or polyacrylonitrile, or thermosetting plastics such as epoxy resins, polyurethane resins, or phenol resins. The sample unit and the substance container are preferably manufactured by injection molding processes, but can also be manufactured by additive production techniques such as 3D printing, or sintering, lamination, extrusion, adhesive bonding, milling, cutting, or ablation.

The sealing film or sealing plate for sealing the reservoir typically consists of a water impermeable or air impermeable material, in particular a metal, for example aluminum, or a non-elastic plastic, i.e. a plastic having a modulus of elasticity greater than 0.1 GPa at 20° C. The thickness of the sealing film or sealing plate typically amounts to between 10 μm and 200 μm, preferably between 20 μm and 100 μm. The sealing film or sealing plate can, for example, be adhesively bonded, laminated, or welded to the margins of the opening to seal the opening in the reservoir.

In a method of taking up and handling a liquid sample and a substance, a liquid sample is taken up by a sampler that is arranged at a sample unit and a substance container is provided in which a substance is stored in a reservoir. An opener that is arranged at the sample unit is subsequently introduced into an opening of the reservoir that is closed by a sealing film or sealing plate. In this respect, a surface at the opener that is arranged in the direction of the sealing film or sealing plate is aligned at an oblique angle to the surface of the sealing film or sealing plate on contact with the sealing film or sealing plate and raises the sealing film or sealing plate successively from the opening of the reservoir so that an outlet is formed through which the substance can exit the reservoir and is miscible with the sample of the sampler.

The method described can in particular be carried out using the device described, that is the device described is configured to carry out the described method.

DESCRIPTION OF THE FIGURE

Embodiments of the invention are shown in the drawings and will be explained in the following with reference to FIGS. 1 to 10.

There are shown.

DETAILED DESCRIPTION

Figure 1:
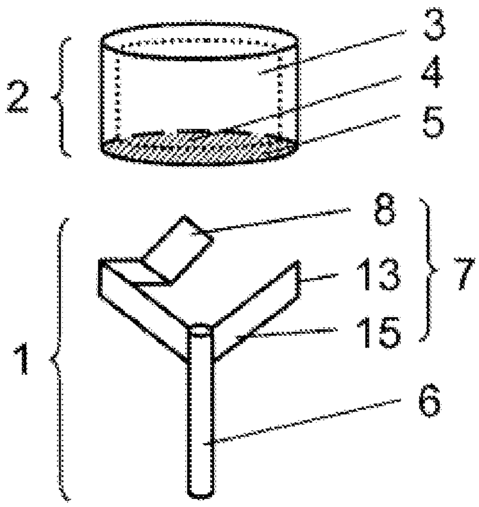
FIG. 1 in a schematic side view, an example of a device in accordance with the invention.
Figure 2:
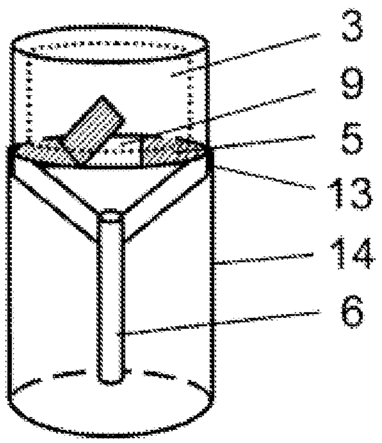
FIG. 2 in a view corresponding to FIG. 1, an example of a device in accordance with the invention in accordance with a possible use.

In FIGS. 1 and 2, an embodiment of a device for taking up and handling a liquid sample is shown in a schematic side view. FIG. 1 shows the device in the dismantled state prior to its use and FIG. 2 shows the device in an assembled state after a possible use.

The device is equipped with a sample unit 1 and a substance container 2. The substance container 2 has a reservoir 3 that is configured to store a substance in the reservoir 3. This reservoir 3 is provided with an opening 4 that is closed by a sealing film or sealing plate 5 so that the substance stored in the reservoir 3 is sealed with respect to the environment and remains in the reservoir 4. The reservoir 3 is thus a cavity closed by the sealing plate 5. The sample unit 1 has an opener 7 and a sampler 6 that is designed to take up and hold a liquid sample. The opener 7 of the sample unit 1 is configured to be at least partially or completely introduced into the opening 4 of the reservoir 3 and to raise the sealing film or sealing plate 5 from the opening 4. In this respect, a surface 8 of the opener 7 that is arranged in the direction of the sealing film or sealing plate 5 and that is introduced into the opening 4 of the reservoir 3 and raises the sealing film or sealing plate 5 from the opening 4 is configured such that the surface 8 is aligned at an oblique angle, i.e. in particular at an angle differing from 0° and 90°, to the surface of the sealing film or sealing plate 5 on contact with the sealing film or sealing plate 5 and raises the sealing film or sealing plate 5 successively from the opening 4 on the introduction into the opening 4 so that an outlet 9 that increases in size on an increasing penetration of the opener 7 is formed in the sealing film or sealing plate 5 through which the substance exits the reservoir 3 and is miscible with the sample of the sampler 6.

The sealing film or sealing plate 5 can be cut successively, i.e. gradually, by the oblique angle between the surface 8 of the opener 7 and the sealing film or sealing plate 5 without tearing in an uncontrolled manner from the margin of the surface 8 and can be raised as a contiguous surface from the opening 4 of the reservoir 3. In the example shown, the angle on a contact of the opener 7 with the sealing film or sealing plate 5 amounts to 45°, but smaller angles than 45°, preferably between 5° and 30°, particularly preferably between 5° and 20°, can also be provided.

The reservoir 3 of the substance container 2 can typically contain a volume of 0.5 ml to 5 ml. The reservoir 3 can, as shown in FIGS. 1 and 2, be configured as a cavity open at one side, with the opening 4 of the reservoir 3 being able to be located at the lower side of the substance container 2 so that the substance can exit the reservoir 3 by means of gravity without impediment on the opening of the sealing film or sealing plate 5. The opener 7 in the example shown is accordingly introduced into the opening 4 of the reservoir 3 from below or the substance container 2 is placed on the sample unit 1 from above to establish a contact between the opener 7 and the sealing film or sealing plate 5 and to raise the sealing film or sealing plate 5 successively from the opening 4 of the reservoir 3.

The sample unit 1 and the substance container 2 preferably consist of chemically inert plastics, polypropylene in the example shown of FIGS. 1 and 2.

The substance container 2 or the sealing film or sealing plate 5 particularly preferably consist of thermoplastics so that, on the application of the sealing film or sealing plate 5, only the sealing film or sealing plate 5 or the substance container 2 around the opening 4 of the reservoir 3 are heated and no additional adhesives are required. The sealing film or sealing plate 5 can, however, also be adhesively bonded to or laminated on the substance container 2 by means of a chemically inert adhesive for the provision of temperature sensitive substances or for the use of substance containers 2 of, for example, thermosetting plastics.

The opening 4 of the reservoir 3 in the example shown of FIGS. 1 and 2 is closed by a sealing film 5 of aluminum that has a thickness of 20 μm and that is welded to the margin of the opening 4 while pressing. Instead of an aluminum film, other non-elastic materials, in particular plastics, can also be used for the sealing film or sealing plate 5 provided that they are chemically inert and are not permeable for the substance and for air or water. The thickness of the sealing film or sealing plate 5 is selected here such that the sealing film or sealing plate 5 can already be cut by the opener 7 by a manually exerted pressure on the sample unit 1 or the substance container 2 and can be raised from the opening 4 in the reservoir 3.

In the example shown of FIGS. 1 and 2, the sampler 6 is fixedly connected to the opener 7 via narrow webs 15 and forms a unit with the opener 7, that is it is formed with it in one part or in a connection with material continuity. Provision can, however, also be made that the sampler 6 is releasably connected to the opener 7, e.g. via a plug-in connection.

The sampler 6 at the sample unit 1 can be configured, as shown in FIGS. 1 and 2, such that the sampler 1 is arranged disposed opposite the outlet 9 formed by the opener 7, that is, is in particular arranged centrally at the sample unit 1. In this arrangement, the substance can flush the sample out of the sampler 1 on exiting the reservoir 3. This is of particular advantage for liquid or dissolved substances that are mixed with the sample in a subsequent analysis step. Provision can, however, also be made that the sampler 6 is not arranged centrally in a plan view, but rather laterally offset at the sample unit 1 to e.g. prevent a blocking of the sampler 6 or too high a flow resistance in the outlet direction of the substance.

As shown in FIGS. 1 and 2, the sampler 6 can be configured, for example, as a capillary tube that takes up and holds a defined volume of a liquid by means of capillary forces on contact with this liquid. Such a passive sampler 6 without electronic or mechanically moved elements is fail-safe, inexpensive, and simple to operate. Typical diameters and capacities of the capillary tubes amount to between 0.02 mm and 2 mm or 1 μl to 100 μl. The ends of the capillary tubes can be configured as planar surfaces extending perpendicular to the longitudinal axis of the capillary tube for a very precise volume measurement of the sample, with one end of the capillary tube projecting out of the sample unit 1, as shown in FIGS. 1 and 2, for the taking up of the liquid sample.

In the example of FIGS. 1 and 2, the device also has a connection point 13 for a container 14. The connection point 13 is formed at an oppositely disposed outer surface of the opener 7 so that a container 14 can be fastened thereto that surrounds the opening 4 of the reservoir 3 and the sampler 6. The container 14 can, as shown in FIG. 2, be placed onto the sample unit 1 and can seal the sample in the sampler 6 toward the environment by friction locking. Instead of a plug-in connection, a connection point 13 for a screw connection, a latch connection, or a snap-in connection can also be provided, for example. The connection point 13 is preferably designed such that the device can be connected to standard laboratory vessels such as cuvettes, vessels having a standard ground joint, centrifuging tubes, or Eppendorf vessels, can in particular be placed on or into an opening of these vessels or can be connected to laboratory devices that have a connection point for standard laboratory vessels.

Figure 3:
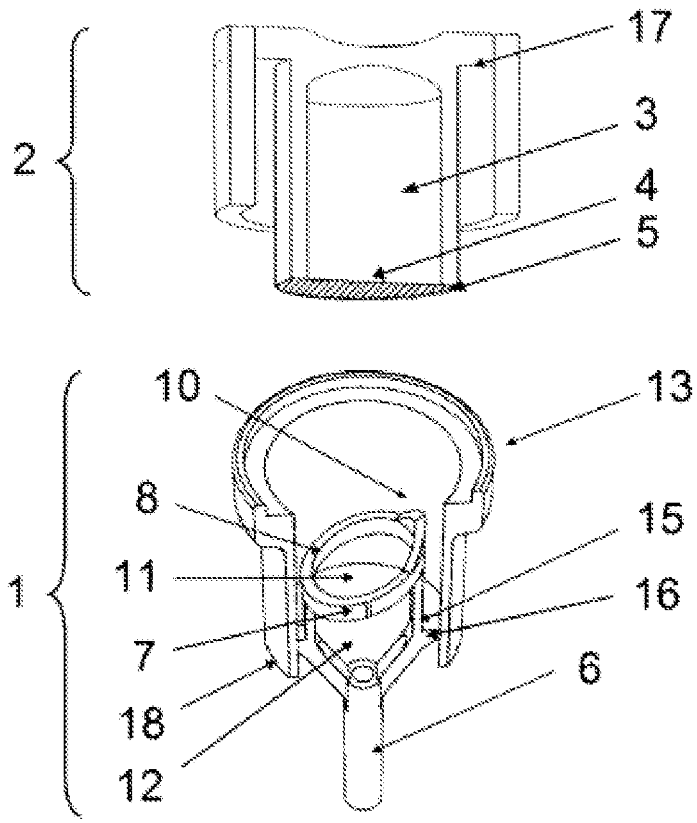
FIG. 3 in a schematic side view, a partial sectional view of a further example of a device in accordance with the invention.

FIG. 3 shows a further example of a device in a schematic partially sectional side view. Recurring elements are provided with identical reference numerals in this Figure and also in the following Figures. In the device of FIG. 3, the surface 8 of the opener 7 that is introduced into the opening 4 of the reservoir 3 and raises the sealing film or sealing plate 5 from the opening 4 is configured such that the surface 8 successively raises the sealing film or sealing plate 5 from the opening 4 of the reservoir 3 staring from the margin of the opening 4 on the introduction into the opening 4. The surface 8 is configured such that its distance from the sealing film or sealing plate 5 on the introduction of the opener 7 into the opening 4 of the reservoir 3 has the smallest distance from the sealing surface of the sealing film or sealing plate 5 at the inner margin of the opening 4. At the point that forms the smallest distance from the sealing surface of the sealing film or sealing plate 5 on the introduction of the opener 7 into the opening 4, the opener 7 moreover has a piercer 10 that pierces the sealing film or sealing plate 5 on the first contact of the opener 7 with the sealing film or sealing plate 5 and thus facilitates the opening of the sealing film or sealing plate 5. A random tearing of the sealing film or sealing plate 5 can in particular be prevented by the piercer 10. Alternatively or additionally, the surface 8 can have a cutting edge at the outer margin that facilitates the opening of the sealing film or sealing plate 5 so that only a small manual pressure has to be applied to penetrate the sealing film or sealing plate 5.

The opener 7 is moreover configured in the direction of the opening 4 at least with a length such that the surface 8 completely penetrates the sealing film or sealing plate 5 on the introduction into the opening 4 after the first contact of the opener 7 with the sealing film or sealing plate 5. In the example of FIG. 3 shown, the reservoir 3 has a circular opening 4. The opener 7 is shaped as complementary to this opening 4, i.e. it can be introduced into the opening 4 with an exact fit. The length of the opener 7 in the direction of the opening 4 amounts to a minimum length that corresponds to the quotient from the sine of the angle that the surface 8 of the opener 7 and the sealing film or sealing plate 5 form on contact of the surface 8 with the sealing film or sealing plate 5 and to the diameter of the opener 7 of the opening 4 so that the surface 8 of the opener 7 can completely penetrate the sealing film or sealing plate 5 on the introduction into the opening 4 starting from the margin. The minimum length of the opener 7 thus corresponds to the minimum penetration depth of the opener 7 into the opening 4 or into the reservoir 3 after the first contact of the opener 7 with the sealing film or sealing plate 5.

The opener 7 is preferably formed with a length in the direction of the opening 4 by which the opener 7, after the sealing film or sealing plate 5 has been completely penetrated by the surface 8, can be introduced so far into the opening 4 or into the reservoir 3 that the opener 7 moves the cut sealing film or sealing plate 5 at the inner wall of the opening 4 or of the reservoir 3 and fixes it there. This has the advantage that the outlet 9 cannot be closed by the loose sealing film or sealing plate 5 on the discharge of the substance from the reservoir 3. The length of the opener 7 preferably amounts to said minimum length for the complete penetration of the sealing film or sealing plate 5 plus at least 50%, particularly preferably 75%, of the inner diameter of the opening 4 or, with non-round openings 4, of the longest distance between the inner walls of the opening 4 or of the reservoir 3.

In the example shown, the opener 7 is formed as a ring having two narrow webs 15 that connect the opener 7 to the sampler 6, with the webs 15 contributing to the length of the opener 7 in the direction of the opening 4. Two lateral outlet openings 12 are formed at the opener 7 by the webs 15 through which outlet openings 12 the substance can exit in the direction of the successively formed outlet 9. The opener 7 additionally has a passage 11 through which the substance can additionally exit the reservoir 3 in the direction of the outlet 9. The flow resistance of the opener 7 is thus very small and the substance can exit the reservoir 3 therethrough both from a lateral direction with respect to the outlet 9 and from a vertical direction with respect to the outlet 9 so that the reservoir 3 can be emptied fast and completely.

An outer contour of the webs 15 is shaped in a complementary manner to the side wall of the opening 4 and of the inner wall of the reservoir 3. One of the webs 15 is moreover arranged in a region in which the surface of the opener 7 has a maximum distance from the opening 3 on the first contact with the sealing film or sealing plate 5. The sealing film or sealing plate 5 can thereby be moved or folded over on the introduction of the opener 7 into the opening 4 to the side wall of the opening 4 and the inner wall of the reservoir 3 and can be fixed there by this web, that is the shorter of the two webs 15 in FIG. 3.

The sample unit 1 of the device in FIG. 3 is furthermore designed with a jacket 18 or a sleeve that is connected to the opener 7 via further narrow webs 16. The jacket 18 surrounds the opener 7 and is open in the direction of the sampler 6 and of the surface 8 of the opener 7 that is introduced into the opening 4 of the reservoir 3. The inner surface of the jacket 18 is formed contoured in a complementary manner to an outer surface of the substance container 2 that is formed around the opening 4 in the reservoir 3 so that the jacket 18 seals the substance container 2 with a force fit or friction locking at this surface on the introduction of the opener 7 into the opening 4 of the reservoir 3. Beside this surface, even further sealing surfaces 17 can be provided at the jacket 18 or at the substance container 2, at which sealing surfaces 17 the substance container 2 and the sample container 1 can optionally be sealed toward the environment by additional sealing material. The jacket 18 of the sample unit 1 on the one hand protects the opener 7, in particular pointed or sharp-edged regions of the opener 7, from unwanted contacts on use and on the other hand provides a holding surface by its outer surface for the handling of the sample unit 1 on the taking up of a liquid sample by the sampler 6. The jacket 18 furthermore has a peripheral connection point 18 for the fastening of a laboratory vessel. The sampler 6 projects out of the sample unit 1 for the taking up of a liquid sample and is formed in the example shown with a concavely arched end surface at the end that projects from the sample unit 1.

Figure 4:
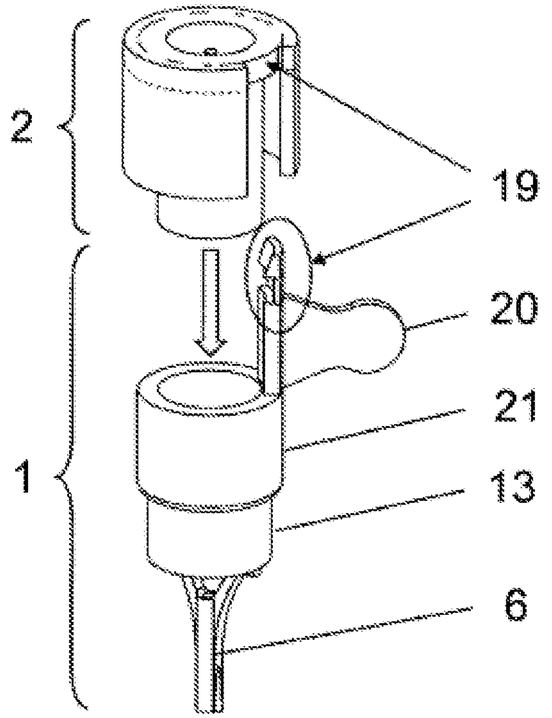
FIG. 4 in a view corresponding to the lower part of FIG. 3, an example of a device in accordance with the invention in accordance with an open snap-in fastening.
Figure 5:
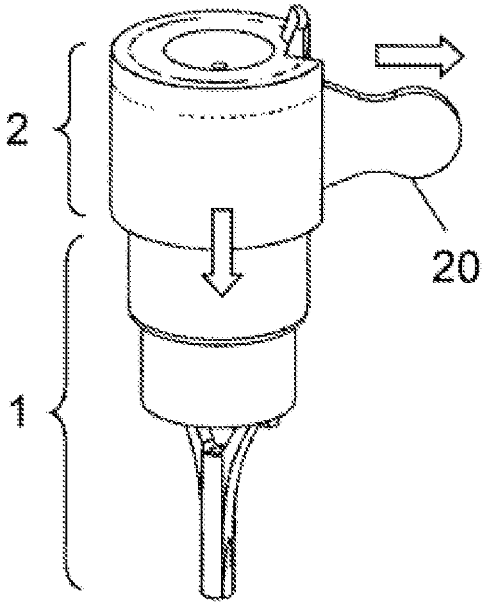
FIG. 5 in a schematic perspective view, an example of a device in accordance with the invention with a closed snap-in fastening before the opening of the sealing film or sealing plate.
Figure 6:
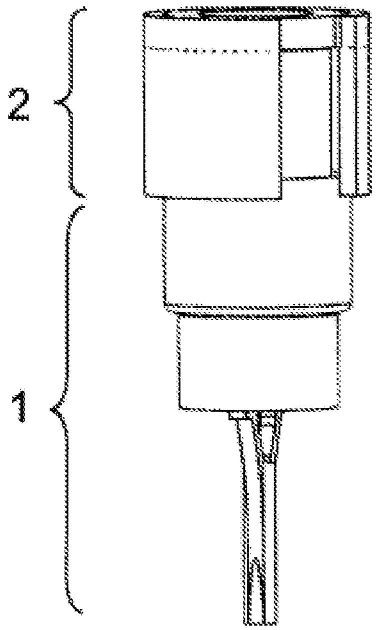
FIG. 6 in a schematic side view, an example of a device in accordance with the invention with a released snap-in fastening after the opening of the sealing film or sealing plate.

A further example of a device is shown in schematic side views in FIGS. 4, 5, and 6. The device inter alia has the features of the device of FIG. 3. For a simple handling of the device, the substance container 2 is moreover fastenable to the sample unit 1 and the substance container 2 and the sample container 1 are configured to introduce the opener 7 into the opening 4 of the reservoir 3 only by means of a pressure on the substance container 2 to raise the sealing film or sealing plate 5 from the opening 4.

FIG. 4 shows the device in the dismantled state prior to its use. The sample unit 1 has a fastening device 19 and a release device 20. The fastening device 19 is releasably fastenable to the substance container 2 by means of a snap-in hook or a latching head. The snap-in hook or latching head in the example shown is arranged at the jacket 18 of the sample unit 1 that surrounds the opener 7. The substance container 2 is pushed, as indicated by an arrow in FIG. 4, onto the sample unit 1 for fastening such that the opener 7 is positioned at the opening 4 of the reservoir 3 and the snap-in hook latches at a margin of the substance container 2 before the opener 7 can contact the sealing film or sealing plate 5 in the opening 4 of the reservoir 3. The sample unit 1 can for this purpose, for example, be held at the holding surface 21 of the jacket 18 that is set back from the connection point 13.

In FIG. 5, the device is shown in an assembled state with a closed fastening device 19 prior to the opening of the sealing film or sealing plate 5. The snap-in hook is latched with shape matching into the groove at the margin of the substance container 2 provided for this purpose and the substance container 2 is fastened to the sample unit 1. The snap-in hook can, for example, be released or removed from the groove at the substance container 2 by a pulling at the pulling tab of the release device 20, as indicated by the arrow in FIG. 5, so that the relative movement of the substance container 2 toward the sample unit 1 is released and the substance container 2 can, as indicated by the arrow, be pushed into the sample unit 1, with the opener 7 opening the sealing film or sealing plate 5 of the reservoir 3 by a single vertical movement. FIG. 6 shows the device of FIGS. 4 and 5 corresponding to a released snap-in fastening after the opening of the sealing film or sealing plate 5.

Figure 7:
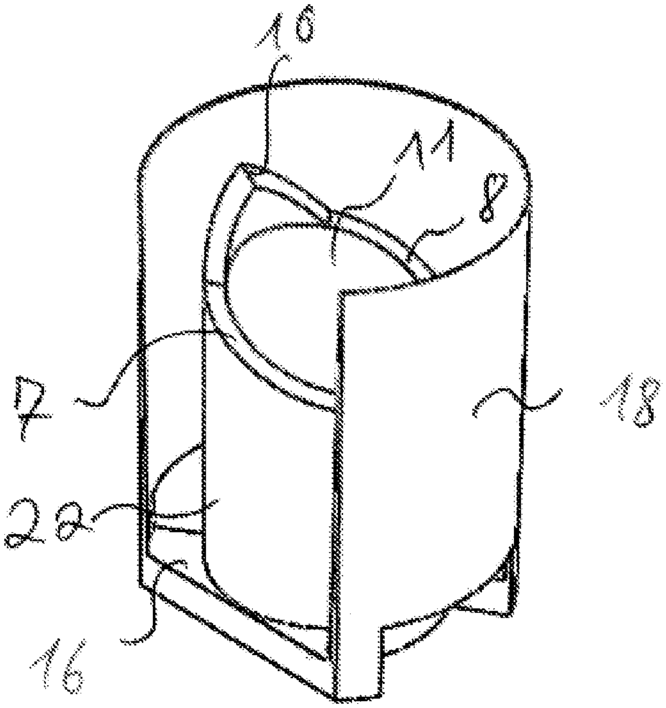
FIG. 7 in a schematic perspective view, an example of an opener configured as a hollow cylinder chamfered at one side.

An embodiment is shown in a schematic perspective view in FIG. 7 in which the basic concept of the embodiment shown in FIG. 3 is used, but with the opening 7 now not being formed as a ring having a comparatively small diameter, for example with just a height of the piercer 10 or less, but is rather formed as a hollow cylinder chamfered at one side. As in the embodiment shown in FIG. 3, the opener 7 is completely surrounded by the jacket 18 that is partially not drawn in the representation of FIG. 7 for the better illustration of the setup. A chamfered surface of the opener 7 is designed, as in the embodiment shown in FIG. 3; instead of the webs 15 that extend in parallel with the jacket 18 and that are typically arranged vertically in use, a jacket surface 22 of the hollow cylinder is now provided, however, that completely surrounds an inner space of the opener 7. The opening 7 is located centrally in the opener 7 and is surrounded by the jacket surface 22.

The jacket surface 22 in the embodiment shown in FIG. 7 is connected to the jacket 18 via two webs 16 that are arranged in a plan view of the piercer 10 offset thereto by 90° or 270°. The jacket surface 22, the webs 16, and the jacket 18 are here formed in one part or in one piece with one another. At the lower end, two through holes are provided in the region of the piercer 10 and disposed opposite the piercer 10, i.e. an intermediate space covered by one of the two webs 16. The webs 16 are so wide in this embodiment that at least one quarter of an intermediate space between the jacket surface 22 and the jacket 18 is covered or overlapped by one of the webs 16. The webs 16 in the embodiment shown are formed from the same material as the opener 7 and in one part or one piece with the opener.

Figure 8:
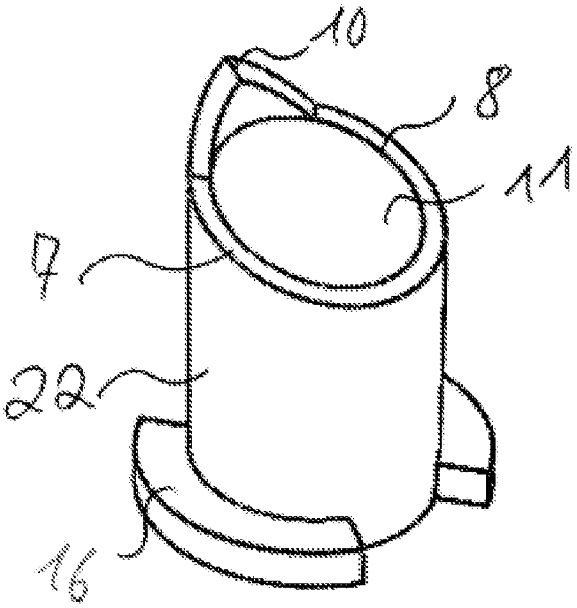
FIG. 8 a view corresponding to FIG. 7 of the opener shown in FIG. 7 without a jacket.
Figure 9:
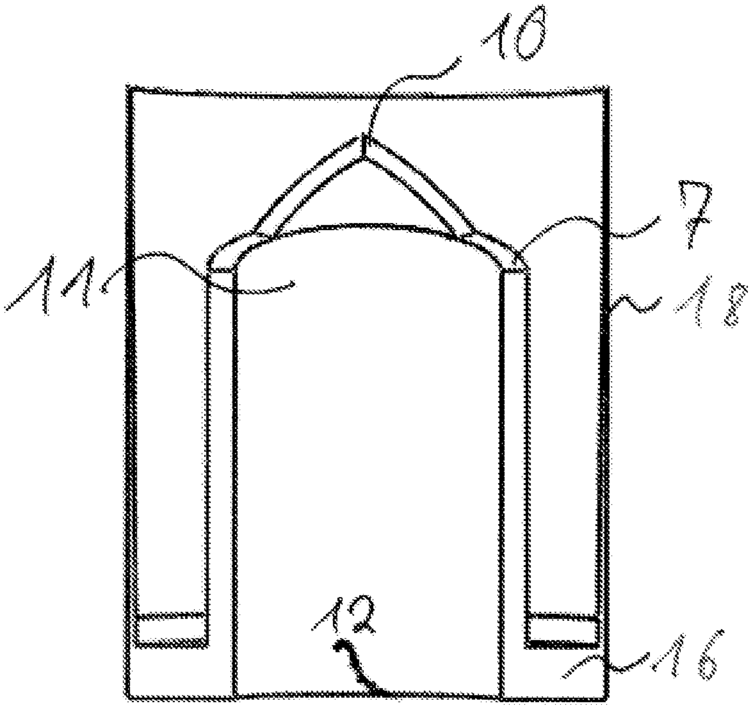
FIG. 9 a sectional view of the embodiment shown in FIG. 7.
Figure 10:
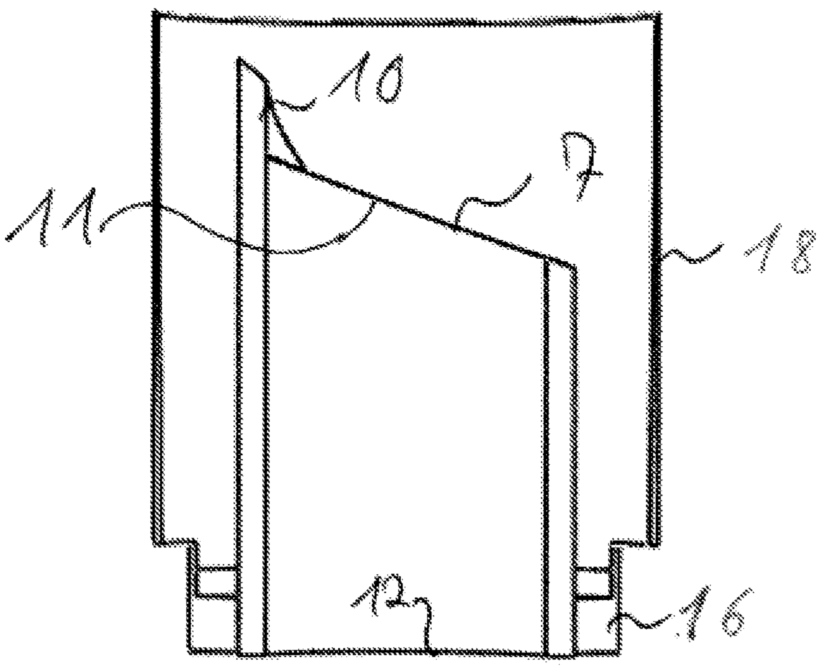
FIG. 10 a schematic sectional view rotated by 90° with respect to the representation in FIG. 9.

In FIG. 8, the opener 7 without the jacket 18 is shown in a view corresponding to FIG. 7. The webs 16 are formed in a manner not completely peripheral around the jacket surface 22 and thus about the opener 7, but rather have the already named cutouts or through holes. FIG. 9 shows the arrangement shown in FIG. 7 in a sectional view from which it becomes clear that a hollow space of the hollow cylinder extends between the opening 11 and the outlet opening 12. In FIG. 10, the arrangement of FIG. 7 is likewise shown in a sectional view, but now the section runs centrally through the piercer 10 along the longitudinal axis of the arrangement, that is rotated by 90° with respect to the sectional view of FIG. 9.

Features of the different embodiments only disclosed in the embodiments can be combined with one another and claimed individually.

The invention claimed is:

1. A device for taking up and handling a liquid sample and a substance having a sample unit and a substance container, in which the substance container has a reservoir that is configured to store the substance in the reservoir;

the reservoir has an opening that is closed by a sealing film or a sealing plate so that the substance is sealed toward an environment in the reservoir;

the sample unit has a sampler and an opener;

the sampler is configured to take up and hold the liquid sample;

the opener is configured to be at least partially introduced into the opening of the reservoir and to raise the sealing film or sealing plate from the opening, wherein a surface of the opener that is arranged in the direction of the sealing film or sealing plate and that is introduced into the opening and raises the sealing film or sealing plate from the opening is configured such that the surface is aligned at an oblique angle to the surface of the sealing film or sealing plate on contact with the sealing film or sealing plate and raises the sealing film or sealing plate successively from the opening on the introduction into the opening so that an outlet is formed in the sealing film or sealing plate through which the substance exits the reservoir and is miscible with the liquid sample of the sampler, wherein the opener is formed as a ring that is connected to the sampler via a first web extending downwardly from the ring, and a second web extending laterally from the first web to a jacket of the sample unit and downwardly to connect with the sampler.

2. The device in accordance with claim 1, wherein the surface of the opener that is introduced into the opening and that raises the sealing film or sealing plate from the opening is configured to raise the sealing film or sealing plate successively starting from a margin of the opening.

3. The device in accordance with claim 1, wherein the opener has a tip, a pricker, a piercer, and/or a cutting edge that cuts the sealing film or sealing plate on contact with the sealing film or sealing plate.

4. The device in accordance with claim 1, wherein the opener is formed as complementary with the opening of the reservoir.

5. The device in accordance with claim 1, wherein the opener has at least one passage and/or at least one outlet opening through which the substance exits the reservoir on the raising of the sealing film or sealing plate.

6. The device in accordance with claim 1, wherein the opener has an outer contour or outer edge that is shaped such that, on the introduction of the opener into the opening, a gap is formed between the outer contour or outer edge of the opener and a side wall of the opening or inner wall of the reservoir in which the sealing film or sealing plate is fixed.

7. The device in accordance with claim 1, wherein the substance container is fastenable to the sample unit and is configured to introduce the opener into the opening via a compressive movement and/or rotational movement at the sample unit or at the substance container and to raise the sealing film or sealing plate from the opening.

8. The device in accordance with claim 1, wherein the sample unit has a connection point at which an additional container is fastenable that surrounds the sampler and the opening of the reservoir.

9. The device in accordance with claim 1, wherein the substance container has a plurality of reservoirs and the sample unit has a plurality of openers.

10. The device in accordance with claim 9, wherein the plurality of openers have different lengths so that each sealing film or sealing plate for each reservoir in the plurality of reservoirs is opened after one another on introductions of the plurality of openers into each opening of each reservoir of the plurality of openings of the plurality of reservoirs.

11. A method of taking up and handling a liquid sample and a substance having a device in accordance with claim 1, in which the liquid sample is taken up by the sampler of the sample unit;

the opener of the sample unit is introduced into the opening of the reservoir of the substance container; and the opener raises the sealing film or sealing plate by which the opening of the reservoir is closed from the opening so that the outlet is formed through which the substance exits the reservoir and is miscible with the liquid sample of the sampler.

* * * * *